United States Patent [19]

Fath et al.

[11] Patent Number: 4,769,017
[45] Date of Patent: Sep. 6, 1988

[54] SELF-SEALING INFUSION MANIFOLD AND CATHETER CONNECTOR

[76] Inventors: John J. Fath, 30429 Lincolnshire, Birmingham, Mich. 48010; Jorgen A. Jorgensen, 10408 Rich Rd., Bloomington, Minn. 55437; Alex L. Darbut, 5908 Tamarac La., Edina, Minn. 55436

[21] Appl. No.: 9,636

[22] Filed: Jan. 29, 1987

Related U.S. Application Data

[63] Continuation-in-part of Ser. No. 720,067, Apr. 4, 1985, abandoned.

[51] Int. Cl.⁴ ............................................. A61M 25/00
[52] U.S. Cl. ...................................... 604/283; 604/83; 604/247
[58] Field of Search ................. 604/83, 167, 245, 247, 604/256, 283, 8–10, 246

[56] References Cited

U.S. PATENT DOCUMENTS

| | | | |
|---|---|---|---|
| 3,416,567 | 12/1968 | Von Dardel et al. | 604/83 |
| 3,463,159 | 8/1969 | Heimlich | 604/247 |
| 3,507,275 | 4/1970 | Walker | 604/246 |
| 3,613,663 | 10/1971 | Johnson | 604/86 |
| 3,618,637 | 11/1971 | Santomieri | 604/83 |
| 3,797,478 | 3/1974 | Walsh et al. | 604/256 |
| 3,861,388 | 1/1975 | Vaughn | 604/86 |
| 3,994,293 | 11/1976 | Ferro | 604/83 |
| 4,103,689 | 8/1978 | Leighton | 604/247 |
| 4,346,704 | 8/1982 | Kulle | 604/247 |
| 4,412,834 | 11/1983 | Kulin et al. | 604/283 |
| 4,447,230 | 5/1984 | Gula et al. | 604/126 |
| 4,447,237 | 5/1984 | Frisch et al. | 604/256 |
| 4,512,764 | 4/1985 | Wunsch | 604/80 |
| 4,657,530 | 4/1987 | Buchwald et al. | 604/247 |
| 4,657,536 | 4/1987 | Dorman | 604/247 |

FOREIGN PATENT DOCUMENTS

| | | | |
|---|---|---|---|
| 2446643 | 9/1980 | France | 604/83 |
| 2056284 | 3/1981 | United Kingdom | 604/83 |

*Primary Examiner*—C. Fred Rosenbaum
*Assistant Examiner*—Gene B. Kartchner
*Attorney, Agent, or Firm*—Douglas L. Tschida

[57] ABSTRACT

An elastomeric member having one or more preformed, self-sealing slits and which and dilate at predetermined pressures to form a fluid flow path. In an undilated condition, reverse flow is prevented.

In various embodiments, an elastomeric infusion manifold is disclosed having a plurality of self-sealing slits formed therein relative to either a center lumen, a center slit or in independent relation to one another. Individual, hole mounting, fingered compression-type clamps permit a one-handed connection to the manifold.

In other embodiments, catheters are disclosed having lengthwise co-extensive self-sealing, flow channels, comprising slit containing core members, integral slit containing solid portions or solid core members mounted within the catheter lumen such that flow occurs in the space between the core and the catheter walls. Conventional leur lock connectors or compression-type clamp connectors are useable therewith. In still other embodiments, catheters with multiple self-sealing fluid vents are combined with drains for irrigation and sumping.

24 Claims, 5 Drawing Sheets

U.S. Patent  Sep. 6, 1988  Sheet 1 of 5  4,769,017
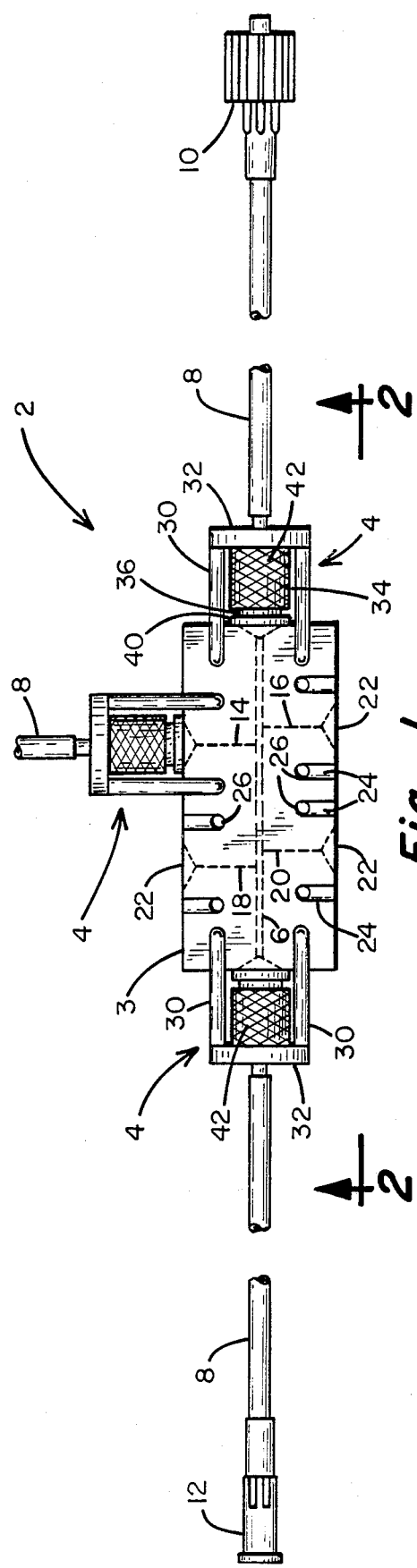
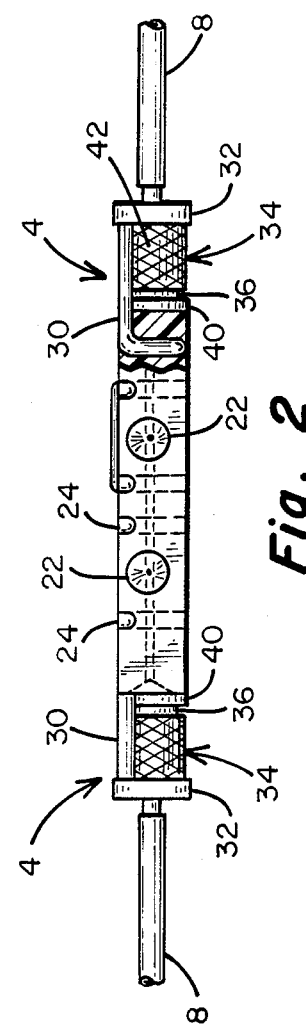
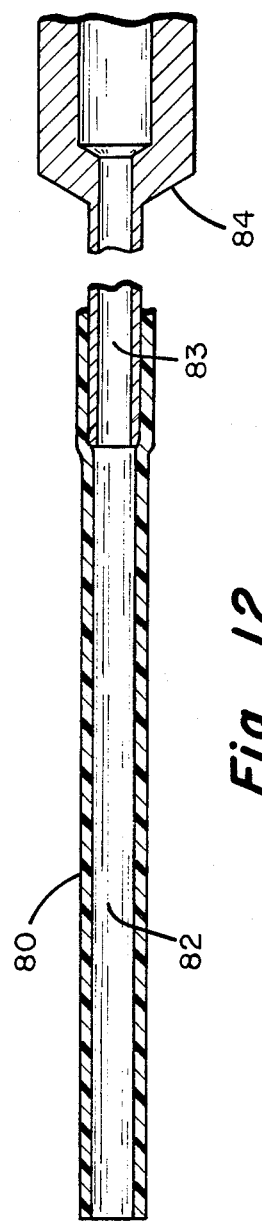

SELF-SEALING INFUSION MANIFOLD AND CATHETER CONNECTOR

This is a continuation-in-part of application Ser. No. 720,067 filed Apr. 4, 1985 now abandoned.

BACKGROUND OF THE INVENTION

The present invention relates to infusion systems and, in particular, to apparatus for obtaining a zero dead volume, self-sealing connection to a primary flow path, whereby medications can be accurately delivered in a bolus fashion without air embolus, clotting and tissue infection.

Patient infusion systems, whether they be of the gravity type of more sophisticated microprocessor controlled pump type, have undergone a number of improvements over the years with a variety of such systems now being able to more accurately control the delivery rate over time and thereby provide a delivery profile tailored to the patient. As these improvements have occurred, however, a number of problems have been recognized and one of which arises where a patient requires a number of simultaneous infusions of different infusants and/or the administration of a variety of medications in combination therewith. In particular, the rate controllers presently available are not able to accommodate multiple infusants, since each rate controller typically takes into account only the delivery of a single infusant, thus requiring multiple controllers for each different infusant. Even where systems can accommodate multiple infusants, unless relatively sophisticated control circuitry is included therewith, they are unable to accurately assure overlapping delivery profiles for each of the individual infusants. Still further, where one of the infusants is a relatively potent medication, concern arises as to the potential combinational effects of the simultaneously delivered infusants, not to mention the need to be able to accurately delivery the medicant in an undilated form so as to provide the desired effect.

For many critically ill patients and/or patients receiving a number of infusants, an additional problem that oftentimes arises is that only a limited number of access sites are available, thus suggesting the desirability of using a single site to infuse multiple medicants.

As mentioned, a primary concern with the infusion of multiple infusants through a single cannula is that of possible combinational reactions between the infusants and which may be harmful to the patient. Typically, infusant compatability, be it between a potent medication and a bulk volume infusant or some other infusant, is determined by mixing the infusants in a sample container and allowing the infusants to interact over time. If a precipitate forms or a deleterious reaction occurs, indicative of incompatability, the infusants are not administered via a single infusion set. Instead, separate infusion sets and access sites are used.

Such an empirical selection technique, however, ignores the realities of medicant delivery and the discontinuous timing at which many infusants are delivered. That is, with many potent medications, they are delivered in substantially a single bolus over a relatively short period of time so as not to appreciably mix with other infusants. Also, it ignores the fact that many potent medications can be administered along with other marginally compatable infusants, if assurances can be had that the infusants will be isolated from one another until they enter the patient cannula.

Some attempts that have been made to develop multiple infusant delivery systems for a single access site can be seen upon directing attention to U.S. Pat. Nos. 3,566,930; 3,618,637; and 4,191,183. In order to overcome the aforementioned problems, the U.S. Pat. No. 3,618,637 suggests a rotary mixing valve, whereby the infusants are controllably selected and delivered. The U.S. Pat. No. 4,191,183, in turn, suggests a common mixing chamber having a transparent, magnifying window for observing the mixing of the infusants and permitting the viewing thereof for possible precipitates.

Relative to the delivery of more potent medicants in combination with other infusants, other attempts have been directed to various syringe compatible devices and which allow the periodic injection of medicants into the primary flow path. Examples of some devices of this type can be seen upon directing attention to U.S. Pat. Nos. 3,613,663; 3,861,388; and 4,184,489. Each of these devices principally achieves this end via self-sealing septum-like structures which permit the introduction of a syringe needle into the primary fluid flow path. While these devices are relatively simple in construction, medicant delivery requires nursing intervention. Also, the devices have limited lives, since multiple punctures diminish the integrity of the septum-like members.

Still other attempts at developing longer lived devices can be seen upon directing attention to U.S. Pat. Nos. 3,416,567; 3,515,166; 4,439,182; and 3,994,293. There, a variety of infusion systems are disclosed having syringe compatible ports for injecting medicants or relatively small volume infusants at a variety of resilient one-way valves that are cooperatively mounted along the length of the primary infusion set. As disclosed, the one-way valves comprise resilient deflectable flappers and/or ball-type mechanisms. Most pertinent to the present invention is a structure disclosed in the U.S. Pat. No. 3,994,293 which discloses a pre-perforated diaphragm that deflects with the administration of a medicant under pressure. As disclosed, however, a Y-type non-purging connection is contemplated and which includes various cavities between the diaphragm and the primary flow path that can trap air and produce air embolus with the administration of the medicant and/or produce coagulation. Also, the disclosed device is not compatible with infusants deliverable by other than a syringe barrel. Furthermore, it contemplates a relatively large slit in a relatively thin diaphragm member, but which would not be tolerant of the higher back pressures encountered for many infusions.

In order to overcome the foregoing problems, the present invention was developed and which essentially comprises an elastomeric manifold member or catheter having one or more preformed self-sealing slits, each slit coupling an associated inlet port to an outlet fluid flow path. Each infusant is thus isolated from any others via a zero dead volume flow path that opens only under the presence of a predetermined pressure. Depending upon the application, the configuration and durometer of the flow paths can be arranged as desired.

The above objects, advantages and distinctions of the present invention, among others, as well as its construction will be described hereinafter with respect to the appended drawings and a number of alternative embodiments. Before referring thereto, however, it is to be recognized that the following description is made with respect to the presently preferred embodiments only and is not intended to be all inclusive in its description, thus it should not in any way be interpreted to be self limiting.

SUMMARY OF THE INVENTION

Infusion apparatus including one or more preformed, self-sealing fluid flow paths formed in an elastomeric member. A pressurized infusant may be delivered via any one of the flow paths, upon achieving a pressure sufficient to dilate the self-sealed path. A number of isolated zero dead volume flow paths isolated from each other are thus obtained.

In one embodiment a plurality of slits are formed in a manifold member relative to a central longitudinally extending lumen. Individual clamp members mate with holes formed in the manifold and compressively secure a contained fluid flow bore in alignment with the lumen and/or one of the preformed slits. Attendant tubing and leur lock connectors attached to the bore of the clamp members permit the coupling of an infusion pump, gravity bag and/or a cannula to the various slits and/or lumen. In use, medicants injected at the preformed slits may thereby be administered through the lumen in bolus doses without incurring deleterious mixing with a primary infusant and without air embolus or coagulation.

In another embodiment, a single lumen, backflow resistant catheter is contemplated. In one version, a solid core member mounted in the lumen of the catheter intermediate a leur lock connector isolates blood flow in the vessel from the infusant and prevents against backflow and possible coagulation in the infusion set. The infusant is delivered by dilating the walls of the catheter adjacent the core member. In a second version, a preformed lengthwise slit is formed in the solid core member.

In still another embodiment, a combination catheter/connector is contemplated wherein a catheter is molded into an elastomeric body member and wherein a solid core portion of elastomeric material extends into the lumen of the catheter. In one version, a preformed lengthwise self-sealing flow path formed in the solid core portion is aligned with an input port and whereat a finger tightened clamp is mountable in alignment therewith. In a second version, infusant flow occurs by dilating the walls of the catheter adjacent a solid core.

Still other embodiments are contemplated wherein the slit containing manifold member includes a rigid plate having a number of holes formed therein for mounting in mating relation to the fingered clamp members so as to interlock with the clamp fingers and add rigidity to the connection. Various other fluid flow slit configurations, pathway combinations and catheter assemblies are also contemplated.

BRIEF DESCRIPTION OF THE DRAWINGS

FIG. 1 shows a top view of a lumen containing manifold, including a plurality of preformed slits opening to the lumen, as well as a number of fingered clamp connectors mounted in alignment with the lumen and slits.

FIG. 2 shows a view along reference lines 2—2 of FIG. 1.

FIG. 12 shows a cross section of a conventional catheter having a solid core of the type of FIG. 11.

DESCRIPTION OF THE PREFERRED EMBODIMENT

Figure 3:
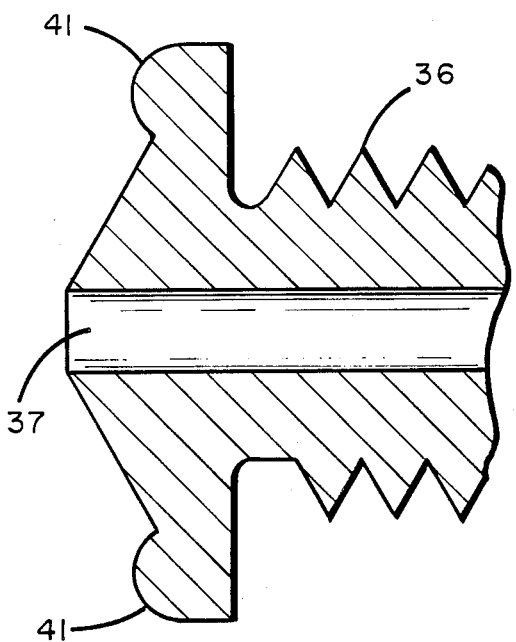
FIG. 3 shows a cross section view through the center portion of a compression fitting having a bossed flange.

Directing attention to FIG. 1, a view is shown of the present infusion manifold 2 relative to a number of clamp connectors 4 that are mounted thereto. Of the clamp connectors 4, the right and left connectors 4 are coupled to the manifold 2 in aligned and clamped relation to a central lumen 6 formed through the manifold 2. In use, the right most clamp 4 via its associated length of tubing 8 and female leur lock connector 10 might, for example, be coupled to a gravity fed infusion apparatus. The left most clamp 4 via its tubing 8 and male leur lock connector 12, in turn, would typically be coupled to a mating leur lock connector containing cannula positioned within an apropriate vessel of the patient. Thus, delivered infusant would pass through the lumen 6 of the infusion manifold 2.

Assuming the above gravity feed configuration, the upper clamp 4 via its associated length of tubing 8 and an appropriate leur lock connector (not shown) is typically coupled to a medication containing infusion pump. A variety of such pump devices are commercially available from a variety of manufacturers with each typically being designed to deliver an operator selected dosage profile of the medicant over time. In the past and where such a pump is used, it typically is coupled to a conventional "Y" type connector in lieu of the present manifold 2. The primary infusant then is most commonly delivered through one branch of the "Y" connector while the medicant is delivered at appropriate times via the other secondary branch of the connector. By using such equipment, however, and upon either piercing the septum of the secondary branch with a syringe and/or coupling the medicant directly thereto, an open fluid path and relatiely long mixing path occurs between the medicant supply and the primary infusion branch. For infusions having relatively high back pressures in the primary infusion branch, this condition then over time causes the contamination of the secondary medicant fluid flow path with the primary infusant and/or possible coagulation therein. By using the present infusion manifold 2, however, the fluid flow path to the medicant supply is isolated from the lumen 6 via the self-sealing preformed slit 14, thus preventing mixing. Similarly, any other medicant or infusant coupled at the manifold 2 to various of the other preformed delivery slits 16, 18 or 20 is isolated from the lumen 6 and mixing is limited to the brief time after the medication is injected through the delivery slit.

Turning attention now to the details of the manifold 2, it is constructed from a medical grade polymer or elastomer, such as silastic or medical grade silicone or any other medically acceptable self-sealing material, having a sufficient durometer to retain a relatiely rigid shape, yet provide self-sealing properties for the slits 14, 16, 18 and 20. In the presently preferred embodiment, it comprises a silastic member 3 that is molded to include a number of conically shaped ports 22 in alignment with the ends of the lumen 6 and the slits 14, 16, 18 and 20. The slits 14, 16, 18 and 20 being formed by inserting a stylus-like member into the manifold 2 at appropriate times during curing to form the self-sealing flow paths. Thus, the slits are presently of a round cross sectional shape, when dilated, although it is to be recognized that other shapes can be used depending upon the desired dilating pressure, material type, etc. Molded also into the manifold 2 in lateral relation to each conical port 22 are a pair of channels 24 that extend inwardly from the edge of the manifold and each of which terminate in a hole 26 that is formed through the manifold 2. The pairs of channels 24 and holes 26 are formed to receive the bent fingers 30 of the clamp members 4, but which will be described in greater detail hereinafter.

Turning attention to FIG. 2, and which shows a view taken along section lines 2—2 of FIG. 1, it is to be noted that the depth of each of the channels 24 is such that when the clamp fingers 30 are received therein, the fingers 30 are essentially surrounded by the manifold 2 so as to provide structural support thereto. Also, the bent portion of the fingers 30 in the holes 26 extend substantially through the manifold 2. This support is particularly important to ensure a positive connection of the infusion set to the manifold 2, without disturbing other connections or inducing misalignment of the connectors 4.

Figure 4:
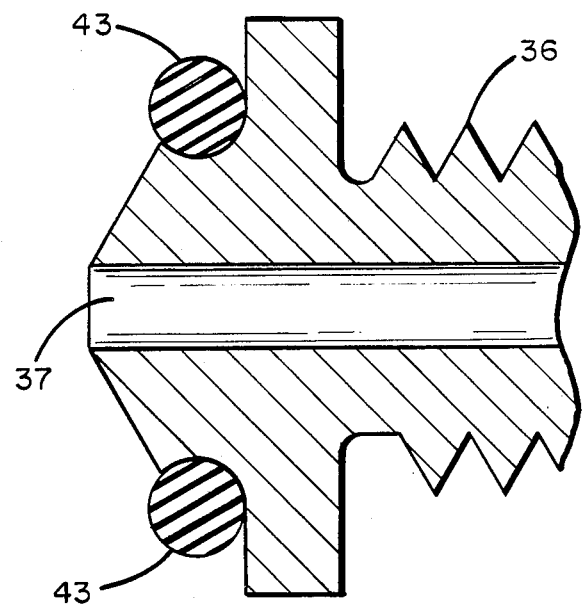
FIG. 4 shows a cross section view through the center portion of a compression fitting having an "O" ring containing flange.

With particular attention to the construction of the connectors 4, each is comprised of a pair of L-shaped fingers 30 that extend from a base plate member 32. In the presently preferred embodiment, the finger members 30 and base plate 32 are constructed from a molded plastic. Mounted to the base plate 32 in concentric relation to the fluid flow path is a two-part brass compression fitting 34. It includes a centrally positioned, fluid flow bore containing threaded portion 36 having a conically shaped fore-end, which mates with the conical ports 22, and a rear-end that mounts through the base plate 32 and receives the tubular member 8 therearound. The longitudinal bore (not shown) formed through the portion 36 provides a fluid flow path through the connector 4. A flat washer-like flange portion 40 surrounding the conical fore-end of the connector 4 abuts against the manifold 2 in surrounding relation to the conical port 22 so as to facilitate the alignment and sealing of the clamp 4 to the manifold 2. It is to be noted that in lieu of a flat flange 40, an annular boss 41 might be formed therein in the fashion of FIG. 3. Alternatively, the flange might be formed to accept an "O" ring seal 43 in the fashion of FIG. 4.

Threadably mounted to the center member 36, in turn, is a thumb actuated screw portion 42 and which has a knurled outer surface to permit the nurse attendant to either screw the member 42 toward or away from the base plate 32 and thereby cause the center bore to be compressively secured to the manifold 2 or released therefrom. Specifically, by screwing the thumb screw portion 42 against the base plate 32, the center bore containing portion 36 is caused to move toward the manifold 2, due to the confinement of the clamp fingers 30 in the manifold 2. Particular advantages is thereby achieved in that a one-handed compressive connection is obtained. The ease is making the connection is particularly advantageous given the variety of personnel using the equipment. Also, the connection is not prone to loosening, due to the counteracting forces. Thus, a simple positively sealed connection is obtained.

Figure 5:
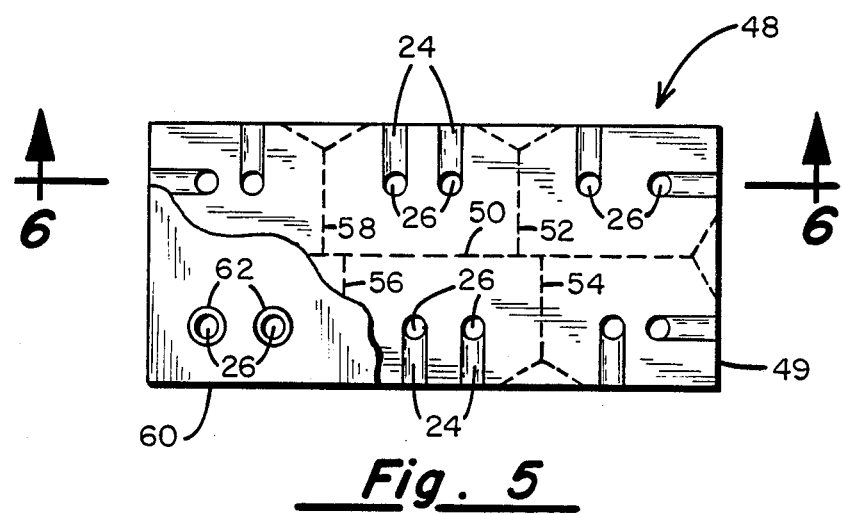
FIG. 5 shows a top view of a manifold in partial cutaway and wherein a mounting plate for strengthening the clamp connection is shown.
Figure 6:
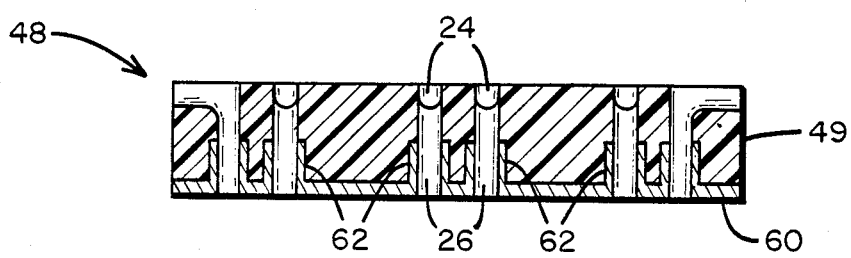
FIG. 6 shows a view along reference lines 6—6 of FIG. 5.

Turning attention next to FIGS. 5 and 6, views are shown of an alternative embodiment of the manifold 2 of FIGS. 1 and 2. Specifically, with attention to FIG. 5, a top view in partial cutaway is shown of a manifold 48 having a center preformed slit 50 as well as a number of intersecting slits 52, 54, 56 and 58 opening thereto. The slit 50 is designed to open at a relatively low pressure in comparison to the slits 52, 54, 56 and 58. This end is achieved by varing the shape and/or size of the slit 50 from the others and/or alternatively molding the manifold 48 in stages with slit containing inserts and/or forming reliefs in the surfaces of the manifold 48 adjacent the slits so as to create different durometers and dilating pressures in the regions of the slits. Thus, the pressure required to open the preformed slits 50, 52, 54, 56 and 58 can be tailored relative to the intended application. In tailoring the pressure characteristics of the manifold 48, care must be had, however, to prevent against undesired flow paths between opposed slits. Consequently, it is anticipated that the center slit 50 would typically open under the lowest pressure. From FIGS. 1 and 5, it is also to be noted that the slits 14 and 18 and 52 and 58 are offset laterally from the respectively opposed slits 20 and 16 and 56 and 54, to prevent against possible flow therebetween.

Figure 7:
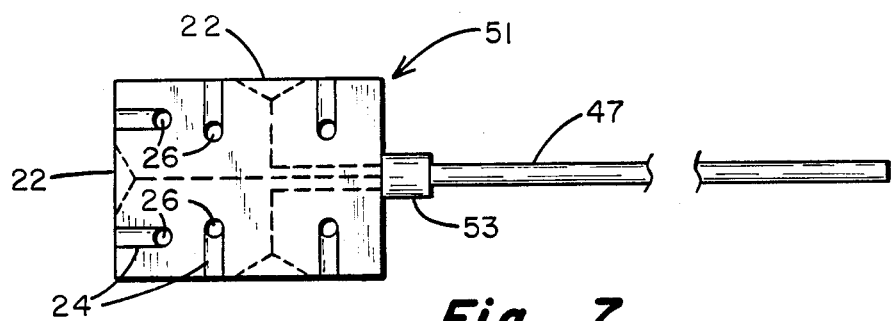
FIG. 7 shows a manifold having a number independent self sealing flow paths.
Figure 8:
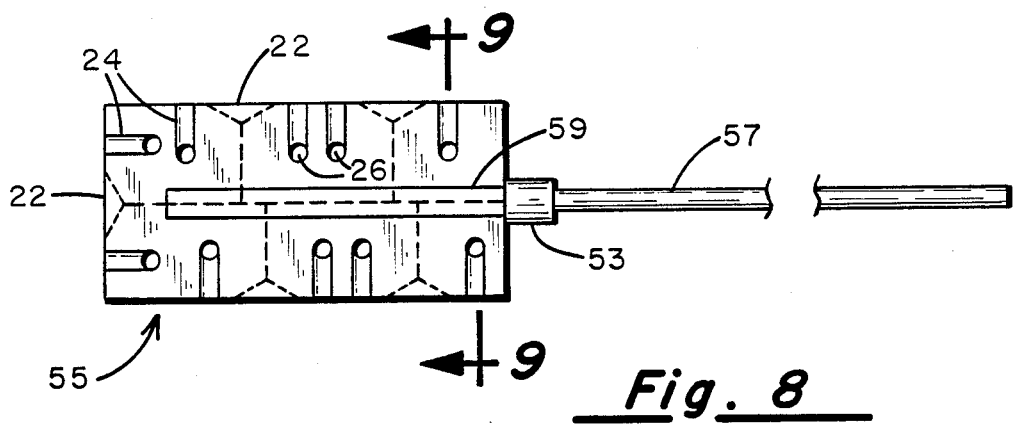
FIG. 8 shows a top view of a manifold having a recess formed along a portion of the length of a longitudinal flow path to vary the durometer thereof.
Figure 9:
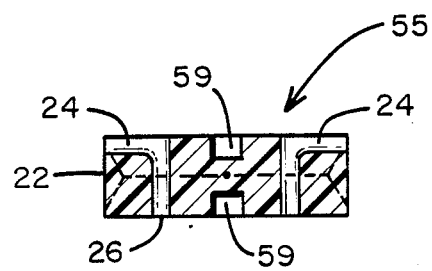
FIG. 9 shows a cross section view taken along section lines 9—9 of FIG. 8.

Examples of some other manifolds having tailored flow paths can be seen in FIGS. 7, 8 and 9. FIG. 7 shows a manifold 51 and integral catheter 47 wherein a number of independent continuous self sealing flow paths are formed and which extend to the distal end of the catheter 47. A protrusion 53 formed intermediate the manifold 51 and catheter acts to frictionally support an introducer (not shown) that is used during the initial insertion of the catheter 47. FIGS. 8 and 9, in turn, show a manifold 55 and catheter 57 having the durometer of the center slit tailored to be less than that of each other slit by forming a recess 59 in the upper and lower surfaces of the manifold 55. Regardless of the pressure at which the infusant is delivered to the manifold 55, the pressure drop at the center slit is such as to prevent against flow in any of the other slits. In this regard, it should also be noted that regardless of the magnitude pressure needed to dilate a self-sealing slit, each manifold and/or catheter is designed so that pressure on the medicant drops substantially in the region adjacent the distal end of the slit so as not to cause discomfort to the patient.

From the cutaway portion of FIG. 5, it is to be noted that a mounting plate 60 is positioned beneath the elastomeric member 49. It includes a number of stand-offs 62 that mount in a portion of the holes 26 and which alignment can better be seen in FIG. 6. The mounting plate 60 is bonded to the elastomeric portion 49 by a suitable adhesive or molding operation and acts to stiffen the member 49 relative to the clamp finger members 30 so as to obtain a rigid connection thereto. Specifically, the clamp finger members 30 extend through the elastomeric portion 49 of the manifold 48 and into the stand-offs 62 so as to obtain support from the base plate 60 when making the compressive connection. Alternatively, the stand-offs 62 may be deleted, and in which case the finger members 30 would be lengthened and the ends of the fingers would have notches formed therein such that the mounting plate 60 would be drawn into the notches, when the clamp 4 is tightened, so as to lock the finger members 30 to the base plate 60 and prevent against inadvertent misalignment or disconnection of the clamp 4.

Figure 10:
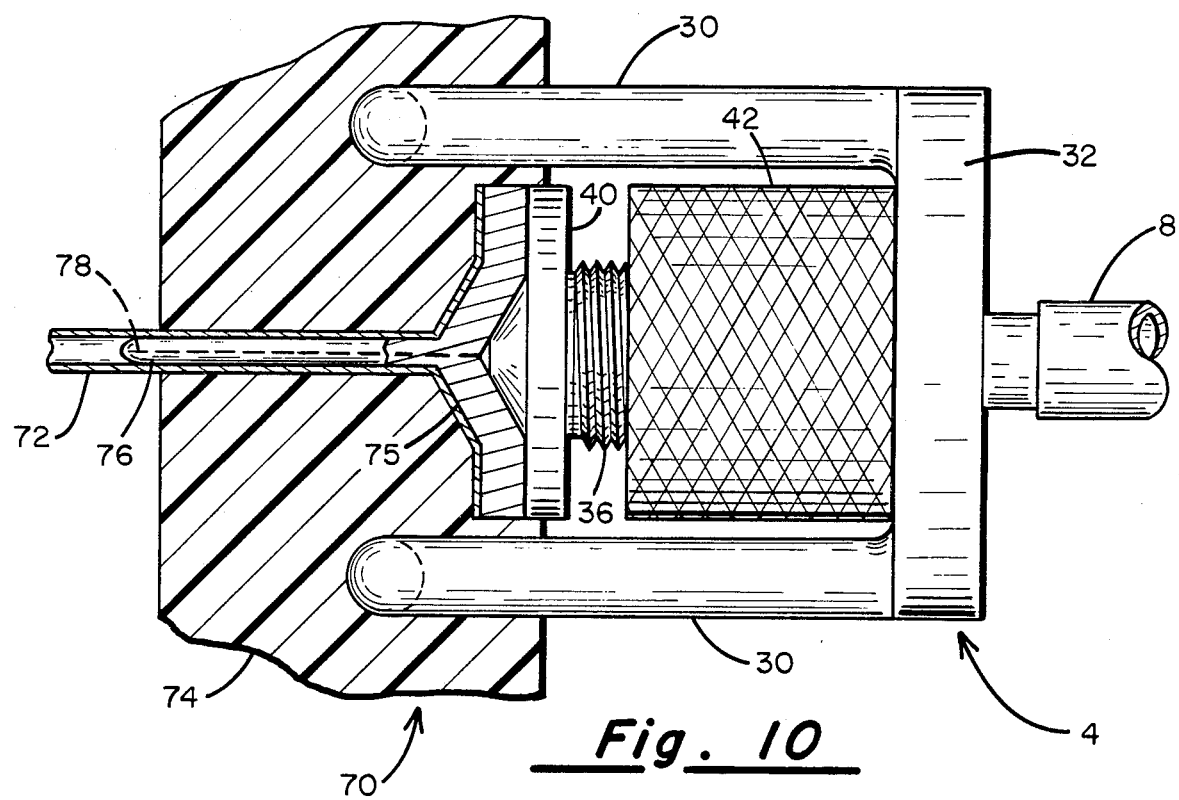
FIG. 10 shows a catheter/connector assembly compatible with the finger clamp connectors and including a solid core.

Turning attention next to FIG. 10, a view is shown of yet another alternative embodiment of the present invention and wherein a catheter/connector assembly 70 having an integrally formed catheter 72 is shown relative to the already described finger clamp assembly 4. Such an assembly might possibly be coupled to the manifold member 2 at its leftmost end in lieu of the male leur lock connector 12. Accordingly, it is contemplated that such a device could be used for making a self-sealing connection to the cannula to prevent against backflow at the connector 70. For this embodiment, the elastomeric body member 74 (only a portion of which is shown) is generally constructed in the same fashion as the previously described manifolds, although it is constructed to be much narrower and accommodate only a single clamp 4. Therefore, only two finger receiving holes 26 are formed in the member 74 relative to a single conical port 75. The connector 4 is aligned relative to the body member 74 in the same fashion as before, upon appropriately turning the thumb screw member 42 relative to the threaded, bore containing portion 36 and base plate 32. Medicant delivered at the tube 8 connected thereto is thus delivered directly to the catheter 72.

In this latter regard, the catheter 72 is molded into the body member 74 in the fashion shown with a conically flared proximal end. A core portion 76 formed from a suitable durometer elastomer and having a preformed longitudinal self sealing slit 78 is then mounted in the catheter 72. The core 76 typically being formed of the same material as the body member 74, but having its length and durometer adjusted relative to a predetermined pressure at which the medicant is to be administered. The core insert 76 can furthermore, either be molded permanently as a part of the catheter connector 70 or be included as a separately mounted insert element, that is slected by the nurse attendant and which would be slip fit into the catheter 72 and body member 74 during assembly. With this latter configuration, and upon changing medications, the attendant can extract and replace the core insert 76 with a new core insert, thus increasing the useable life of the connector 70. As should be apparent, the connector 70 can be coupled to any of the previously described manifolds or used alone with a single infusant. Also, the length of the core insert 76 can be varied as desired.

Figure 11:
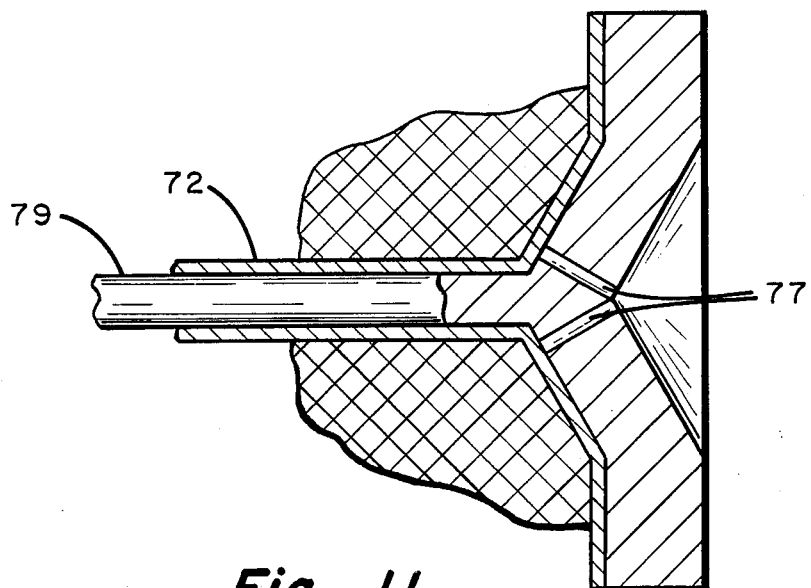
FIG. 11 shows a solid core insert portion for a catheter/connector like that of FIG. 10 wherein the fluid flow path is confined to the space between the catheter walls and the solid core.

FIG. 11 shows a solid core insert 79 for a catheter/connector like that of FIG. 10 wherein a pair of boxes 77 are formed at the proximal end of the insert 79 in the area adjacent the bore 37 of the clamp connector 4. For this embodiment, the pressurized infusant passes through the bores 77 and slightly dilates the walls of the catheter 72 and/or compresses the solid core 79 so that the infusant is directed along the catheter 72 in the space adjacent the catheter walls and the outer surface of the solid core 79. Upon removing the pressure, the catheter walls contract and the catheter 72 is sealed against backflow. The length of the solid core 79 can also be adjusted as desired to ensure a pressure drop before the medicant enters the patient and to prevent against possible coagulation and backflow in the catheter 72.

Turning attention next to FIG. 12, yet another embodiment is disclosed of a more conventional catheter construction. For this embodiment, it is contemplated that during the forming of the catheter 80, a solid core portion 82 of the type described in FIG. 11 would be added in between the lumen containing portion 84 of the catheter and an appropriate leur lock connector (not shown) coupled to the proximal end of the catheter 80. Thus, the catheter 80 would be constructed in a conventional fashion, with the exception of the mounting of the solid core portion 82 distal to the lumen 83. Infusant flow would again occur in the space adjacent the solid core 82 and the catheter walls, when pressurized, with the solid core portion 82 again sealing the distal end of the catheter 80 against possible backflow, coagulation and contamination when not pressurized. Alternatively, it is to be recognized that the catheter/connector of FIG. 12 might include a core portion 82 having a preformed self sealing slit. In either case, the length of the core 82 and the catheter material would be adjusted to dilate at a desired pressure.

Figure 13:
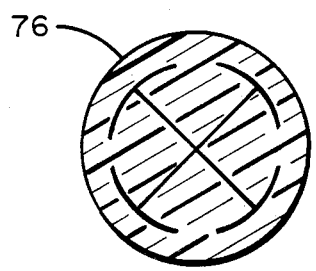
FIG. 13 shows a cross section view through a catheter core member and the shape of one possible slit.
Figure 14:
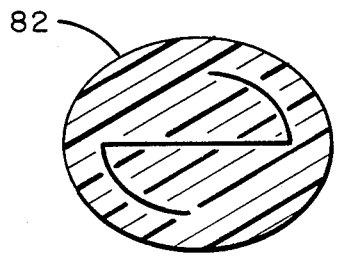
FIG. 14 shows a view like that of FIG. 13, although of an alternative shaped slit.

FIGS. 13 and 14 show two possible slit configurations that might be employed in the core portions 76 and 82 of FIGS. 10 and 12 or for that matter any of the slits. For the core portions, however, and in lieu of a cylindrical, horizontal or vertical puncture slit, the slits may be formed by extruding the core portion over a center mandrel and then turning the core portion inside out so as to assume the slit shape shown. In addition to the slit configurations shown, it is also to be appreciated that a variety of other cross-sectional shapes can be obtained. By selecting an appropriate shape, the pressure characteristic of the core portion can thus be tailored to the length of the catheter and application.

Figure 15:
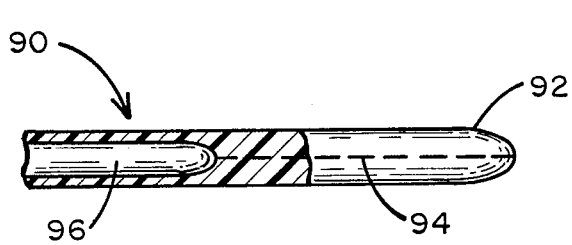
FIG. 15 shows the distal end of a duck-billed catheter having a slit containing solid distal tip.

FIG. 15, disclose a distal solid tip portion of a catheter 90 is shown wherein the tip portion 92 is flattened. In cross section the tip 92 thus has the appearance of a duck-bill. Otherwise, the tip 92 is solid over its length and includes a preformed slit 94 that extends between the lumen 96 and the distal end of the catheter 90. In use it, like the above-described manifolds and catheter/connectors, selectively isolates the infusant from another liquid thereby preventing against backflow and/or coagulation.

Referring lastly to FIGS. 16 and 17, 18-21 and 22-25, a number of alternative embodiments are disclosed of medical drains wherein integrally coextensive self-sealing medicament flow channels or pathways are incorporated into the drain side walls. Each flow channel has a number of self-sealing outlets disposed along its length for distributing medicaments for irrigating the surrounding tissue with germicides and the like and enhancing drainage by preventing tissue and debris from attaching to the drain.

Figure 16:
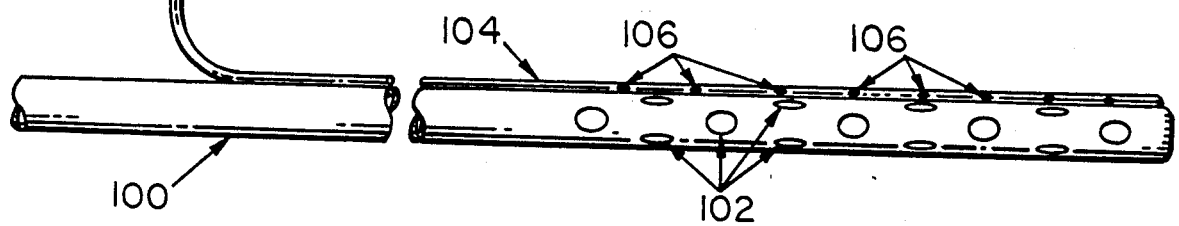
FIG. 16 shows a side elevation view of a round drain including an integral irrigation channel formed into the side wall.
Figure 18:
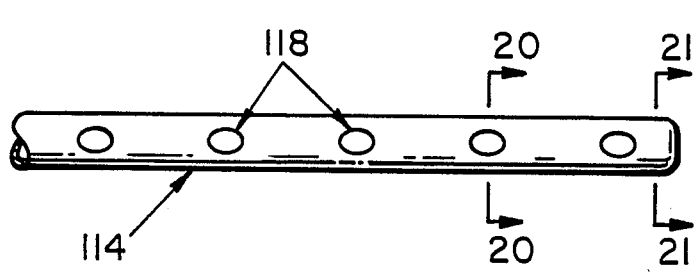
FIG. 18 shows a top plan view of a round drain including opposed irrigation and sump channels incorporated into its side walls.

With attention first directed to FIG. 16, a fore-shortened side elevation view is shown of a conventional round drain 100 modified to include the improvements of the present invention. Such drains 100 (without modification) are commonly used in various procedures for draining away wound fluids which otherwise collect at a wound site. They are commonly precutaneously placed for draining abscesses or surgical wounds. Regardless, however, of the drain and its usage technique, be it wound lavage or an air sumping technique, a variety of problems are oftentimes encountered with currently available drains relative to maintaining a sterile pathway, preventing drain plugging and promoting tissue healing.

To overcome various of these shortcomings, the drain of FIG. 16 provides a self-sealing medicament flow channel or fluid pathway 104 along its length for admitting medicaments to irrigate the surrounding tissue and/or clear the drain lumen 103. In particular, the medicaments are delivered by way of an integrally formed self-sealing flow channel 104 formed in the side wall of the elastomeric drain 100. Alternatively, the flow channel 104 may be separately bonded to the drain. Such medicaments are delivered by way of a leur lock connector 101 to a plurality of self-sealing outlet ports 106 disposed along the length thereof for irrigating the surrounding tissue. Each port 106 opens to an interior self-sealing pathway using either a slit or solid core as described previously. Appreciating that a pressure drop occurs at each outlet port 106, depending upon the application and to ensure a controlled volumetric delivery at each port 106, each port 106 may be incrementally increased in size with increasing distances from the connector 101. Upon applying a sufficiently pressurized medicament, the otherwise self-sealing flow path dilates to administer the medicament over the length of the drain.

Figure 17:
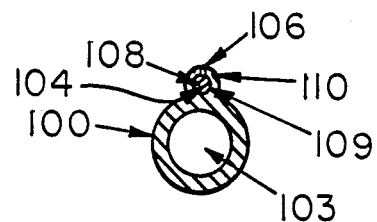
FIG. 17 shows a cross-section view taken along reference lines 17—17 of FIG. 16.

FIG. 17 shows a cross-section view taken along reference lines 17—17 of FIG. 16 and wherein it is to be appreciated that the self-sealing flow channel 104 is achieved via a coextensive solid core elastomeric member 108 positioned within the lumen 109 of the flow channel and against which the interior lumen walls collapse and seal the channel. Each outlet 106, in turn, comprises a self-sealing slit of an appropriate size formed through the drain wall 110. In lieu of directing the slits outwardly to irrigate the surrounding tissue, it is to be appreciated they may alternatively be directed inwardly to enhance the sumping capability of the drain.

In this latter regard, attention is directed to the embodiment of FIGS. 18-21 wherein a round drain 114 is disclosed having an interior lumen 116 which opens to the surrounding tissue at its distal end and at a plurality of apertures 118 provided along the length thereof. Formed coextensively along the drain side walls on opposed sides is a self-sealing irrigation pathway or channel 120 and a self-sealing sump pathway 122. The principal difference between the irrigation and sump pathways 120 and 122 is the direction to which a plurality of self-sealing outlets 124 disposed therealong open. For the irrigation pathway 120, the slits 124 open in the fashion of the slits 106 of Figure 16 to the surrounding tissue, whereas the slits 124 for the sump pathway 122 open interiorly to the lengthwise lumen 116.

Figure 20:
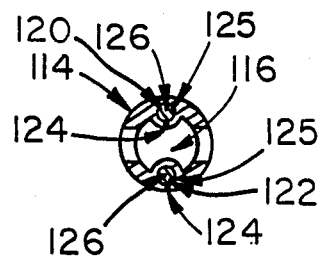
FIG. 20 sows a cross-section view taken along reference lines 20—20 of FIG. 18.
Figure 19:
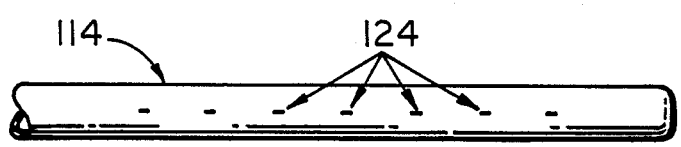
FIG. 19 shows a side elevation view of the drain of FIG. 18.
Figure 21:
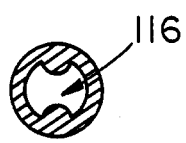
FIG. 21 shows a cross-section view taken along reference lines 21—21 of FIG. 18.

Turning attention to FIG. 19, a side elevation view of the drain 114 is shown and wherein the outlet slits 124 of the irrigation pathway 120 can be seen. The irrigation pathway 120 is shown in phantom. FIG. 20, in turn, shows a cross-section view taken along reference lines 20—20 of FIG. 18 and wherein the solid core elastomeric members 126 can be seen which mount within lumens 125 and which create the lengthwise self-sealing irrigation and sump flow channels 120 and 122. Also shown is one of the self-sealing outlets 124 from each of the irrigation and sump pathways 120 and 122. FIG. 21 shows a cross-section view taken along reference lines 21—21 of FIG. 18 at the drain 114's distal tip and wherefrom it can be better appreciated that the pathways 120 and 122 terminate interiorly of the drain side walls, while the lumen 116 extends to the extreme distal end.

Figure 22:
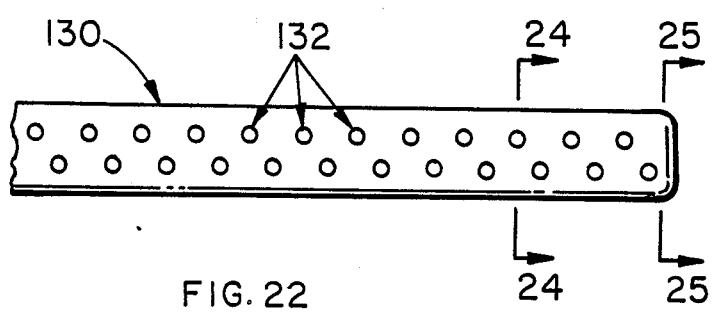
FIG. 22 shows a top plan view of a flat drain including opposed integral irrigation and sump channels formed in the side walls thereof.
Figure 24:
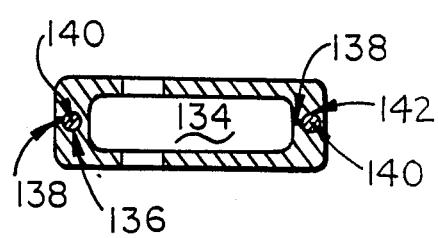
FIG. 24 shows a cross-section view taken along reference lines 24—24 of FIG. 22.
Figure 23:
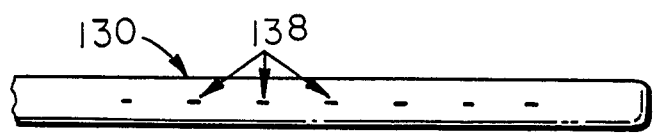
FIG. 23 shows a side elevation view of the drain of FIG. 22.
Figure 25:
FIG. 25 shows a cross-section view taken along reference lines 25—25 of FIG. 22.

Lastly, turning attention to FIG. 22, a top plan view is shown of a flattened, elastomeric drain 130 including a plurality of apertures 132 disposed along the length thereof and interiorly of which a coextensive lumen 134 is positioned to extend to the extreme distal end. As before, opposed irrigation and sump pathways (not shown) are formed in the drain side walls. FIG. 23 shows the irrigation pathway 136 in phantom relative to a plurality of outlet slits 138 disposed along the length thereof. FIG. 24 shows a cross-section view taken along reference lines 24—24 of FIG. 22 and wherein solid core members 140 mounted in the irrigation and sump pathways 136 and 142 can be seen. Also shown are the respective outwardly and inwardly disposed self-sealing outlet slits 138. FIG. 25, in turn, shows a cross-section view taken at the extreme distal end of the drain 130, taken along reference lines 25—25, and wherefrom the earlier termination of the irrigation and sump pathways 136 and 142 can be appreciated.

Even though FIGS. 16-25 disclose solid core member containing irrigation and sump medicament pathways or flow channels, it is to be appreciated that, alternatively, contiguous self-sealing slit pathways comparable to the outlet slits may be employed equally as well.

In summary, the contemplated invention comprises an elastomeric member having at least one preformed slit formed therein which dilates under pressure to form a flow channel and whereby a check valve-like connection is obtained for infusion or other medicament delivery apparatus. Associated connectors couple the self-sealing member to a medicament source and prevent disconnection under the dilation pressures. In one construction, a slit containing manifold permits the connection of multiple medicants and infusants thereto and in another construction provides a direct connection to a cannula, while preventing against backflow. In other catheter constructions it is infusant flow occur along an integral coextensive slit or in a space between a solid member and the walls of the catheter over a portion or the entire catheter length. Still other constructions disclose one or more integral self-sealing outlets formed as part of a drain for irrigating the wound or promoting draining with the delivery of suitable medicaments. From the foregoing, it is therefore to be appreciated that the present invention can be modified in numerous respects to obtain a variety of permutations thereof, without departing from the spirit and scope of the above-described embodiments. Accordingly, it is contemplated that the following claims should be interpreted so as to include all those equivalent embodiments within the spirt and scope thereof.

What is claimed is:

1. Infusion apparatus comprising:
    (a) an elastomeric manifold member having a primary flow channel extending therethrough and including at least one secondary self-sealing flow channel, wherein said secondary flow channel dilates under infusant pressure to form a fluid flow path and opens at one end directly into said primary flow channel and at an opposed end to an exterior surface of said manifold member;
    (b) a plurality of hole pairs extending into said manifold member, the holes of each hole pair extending inward in orthogonal laterally displaced relation on opposed sides of the external opening of each primary and secondary flow channel; and
    (c) at least one clamp means mountable to one of said hole pairs for compressively coupling a fluid flow bore thereof in aligned relation to the external opening of the associated primary or secondary flow channel.

2. Apparatus as set forth in claim 1 including a plurality of secondary self-sealing flow channels and wherein the durometer of the elastomeric material of said manifold member in the region of at least one of said secondary flow channels is tailored to dilate at a fluid pressure different from that at which others of said primary and secondary flow channels dilate.

3. Apparatus as set forth in claim 2 wherein said manifold includes at least one recess in its exterior surface coextensively formed relative to a portion of one of said primary and secondary flow channels whereby the dilating pressure of the adjacent flow channel is determined.

4. Apparatus as set forth in claim 1 including a plate member having a plurality of tubular standoffs projecting therefrom and wherein each standoff is mounted to said manifold member in alignment with one of the holes of each hole pair.

5. Apparatus as set forth in claim 4 wherein said clamp means comprises a body member having first and second L-shaped fingers projecting therefrom for mounting said laterally displaced holes in said manifold member and including a threaded fluid flow bore containing portion having a conical fore-end for mounting in mating relation to an indentation coaxially formed in said manifold member relative to the exterior opening to said flow channel and a screw portion rotatively mounted to said threaded portion for compressively securing said threaded portion to said manifold member upon rotating said screw portion in one direction and for releasing said threaded portion therefrom, upon rotating said screw portion in an opposite direction.

6. Apparatus as set forth in claim 5 wherein said threaded portion includes an annular flange for mounting in abutting sealing relation to the exterior surface of said manifold member about said indentation.

7. Apparatus as set forth in claim 6 wherein said flange includes an annular boss.

8. Apparatus as set forth in claim 6 wherein said flange includes an "O" ring.

9. Apparatus as set forth in claim 5 wherein said indentation conically tapers inwardly from the exterior surface of said manifold member.

10. Infusion apparatus comprising:
    (a) an elastomeric member having at least one self-sealing flow channel, wherein the durometer of said member is selected such that the walls of said flow channel are normally compressively biased to collapse upon themselves to seal said flow channel over its length and to dilate to form a fluid flow path upon exposure to a coaxially applied fluid pressure in excess of a threshold pressure, and wherein at least one mounting hole is provided in said manifold member orthogonally adjacent an external opening to said flow channel; and
    (b) clamp means securable to said mounting hole for compressively coupling a fluid flow bore thereof in aligned relation to said flow channel.

11. Apparatus as set forth in claim 10 wherein said clamp means includes a body member through which said fluid flow bore passes and a finger member securable in said mounting hole.

12. Apparatus as set forth in claim 10 including:
    (a) an elongated catheter having at least one fluid flow path coextensively formed therein; and
    (b) means connecting said catheter to said manifold member and said manifold flow path in flow communication with said catheter flow path.

13. Apparatus as set forth in claim 10 wherein a recess is formed in the exterior surface of said manifold member in coextensive relation to a portion of said flow channel.

14. Infusion apparatus comprising:
    (a) an elastomeric manifold member having at least one flow channel extending therethrough;
    (b) a plurality of hole pairs extending into said manifold member, the holes of each hole pair being laterally displaced on opposed sides of each flow channel; and
    (c) at least one clamp means having first and second L-shaped fingers mounting in one of said hole pairs and including a threaded fluid flow bore containing portion mounting in coaxial mating relation to an opening to said flow channel and a screw portion securing said threaded portion to said manifold member upon rotating said screw portion in one direction and releasing said threaded portion therefrom, upon rotating said screw portion in an opposite direction.

15. Drain apparatus comprising an elongated tubular member including a lengthwise bore extending from a proximal to a distal end, a plurality of apertures extending through the walls of said member in communication with said bore, and at least one medicament delivery channel coextensive over a substantial length of said bore, wherein the walls of said channel normally collapse upon themselves to seal said channel over its length and dilate upon the coupling of a medicament thereto at a pressure sufficiently large to overcome the resilient bias of the channel walls, said channel further including a plurality of self sealing outlet ports radiating from and in flow communication with said channel.

16. Apparatus as set forth in claim 15 wherein said outlet ports are directed exteriorly of said member.

17. Apparatus as set forth in claim 15 wherein said outlet ports are in flow communication with said bore.

18. Apparatus as set forth in claim 15 wherein an elastomer core member is coextensively mounted in said channel such that the channel walls seal thereagainst and medicament flow occurs at the interface therebetween.

19. Apparatus as set forth in claim 15 including first and second medicament delivery channels wherein the outlet ports of said first channel open exteriorly of said member and the outlet ports of said second channel are in flow communication with said bore.

20. Apparatus as set forth in claim 15 wherein ones of said outlet ports open to said bore.

21. Apparatus as set forth in claim 15 wherein ones of said outlet ports open exteriorly of said member.

22. Medicament delivery apparatus comprising:
(a) an elongated elastomeric catheter having a coextensive interior flow channel and a coaxially aligned, recessed proximal inlet and distal outlet thereto, wherein the walls of said flow channel normally collapse upon themselves to resiliently seal said flow channel over its length; and
(b) threaded compressive coupling means having a mating fastener portion detachably mounting in abutment with the catheter in the area of said inlet recess and including a fluid flow bore opening to said inlet for securing a pressurized medicament to the catheter capable of dilating said flow channel over its length.

23. Medicament delivery apparatus comprising:
(a) an elongated catheter having a lumen extending from a proximal to a distal end and including a coaxially aligned, recessed proximal inlet and distal outlet thereto;
(b) an elongated core member coextensively mounted in said lumen over the length of said lumen and wherein the walls of said lumen are biased to collapse and seal against said core member over its length; and
(c) threaded compressive coupling means having a mating fastener portion detachably mounting in abutment with the catheter in the area of said inlet recess and including a fluid flow bore opening to said inlet for securing a pressurized medicament to the catheter capable of dilating said flow channel over its length to create a lengthwise flow path through said catheter in the space between the interior lumen wall and core member.

24. Apparatus as set forth in claim 12 wherein said fluid plow path is defined at the interface between a replaceably mountable core member coextensively mounted in a lumen of said catheter.

* * * * *